United States Patent [19]

Washino et al.

[11] Patent Number: 5,580,545
[45] Date of Patent: Dec. 3, 1996

[54] TASTE MODIFIER AND A METHOD OF MODIFYING TASTE

[75] Inventors: Tsutomu Washino, Toyonaka; Kazuhiko Oosaki, Kyoto; Masamitsu Moriwaki, Osaka; Katsumasa Fujii, Takarazuka; Chiyoki Yukawa, Toyonaka; Tatsuo Akai, Osaka; Kenshi Mitsunaga, Higashiosaka, all of Japan

[73] Assignee: San-Ei Gen F.F.I., Inc., Osaka, Japan

[21] Appl. No.: 425,241

[22] Filed: Apr. 14, 1995

Related U.S. Application Data

[63] Continuation of Ser. No. 137,471, Oct. 18, 1993, abandoned.

[30] Foreign Application Priority Data

Dec. 28, 1992 [JP] Japan .................................. 4-359994
Mar. 30, 1993 [JP] Japan .................................. 5-096784
Jul. 22, 1993 [JP] Japan .................................. 5-181666

[51] Int. Cl.$^6$ .............................. A61K 6/00; A23L 1/221
[52] U.S. Cl. .............................. 424/49; 426/536; 514/974
[58] Field of Search ............................... 424/49; 514/974; 426/536

[56] References Cited

U.S. PATENT DOCUMENTS

| | | | |
|---|---|---|---|
| 3,598,841 | 8/1971 | Swift | 549/403 |
| 3,867,541 | 2/1975 | Robbins | 549/403 |
| 4,031,265 | 6/1977 | Guadagni et al. | |
| 4,154,862 | 5/1979 | Guadagni et al. | |
| 4,906,480 | 3/1990 | Kashket | |

FOREIGN PATENT DOCUMENTS

| | | |
|---|---|---|
| 2556109 | 6/1977 | Germany . |
| 50-13568 | 2/1975 | Japan . |
| 56-45912 | 10/1981 | Japan . |
| 58-138363 | 8/1983 | Japan . |
| 88/08256 | 11/1988 | WIPO . |

OTHER PUBLICATIONS

J. G. Sweeney et al., Journal of Agricultural and Food Chemistry, vol. 27, No. 3, Jun. 1979, Washington, US, pp. 467–469, "Suppression of the sweetness of 2',3-dihydroxy-4-methoxydihydrochalcone by alpha-hydroxylation."

Hasegawa, Database WPI, Section Ch, Week 8339, Derwent Publications Ltd., London, GB; Class D13, AN 83–773058. (1983).

Torey, Database WPI, Section Ch, Week 7518, Derwent Publications Ltd., London, GB; Class B03, AN75–29708W. (1975).

Machida et al., Journal of Japanese Agricultural Chemical Society, vol. 62, No. 12, pp. 1777–1779, 1988.

Mizuno et al., Chem. Pharm. Bull., vol. 35, No. 7, pp. 3025–3028, 1987.

Imai et al., Chem. Pharm. Bull., vol. 37, No. 2, pp. 358–362, 1989.

Hand Book of Sensory Evaluation, Union of Japanese Scientists and Engineers, pp. 398–402, 1973.

Daiwa, Database WPI, Section Ch, Week 8148, Derwent Publications Ltd., London, GB; Class B02, AN79–4607B. (1979).

*Primary Examiner*—Nicky Chan
*Attorney, Agent, or Firm*—Greenblum & Bernstein, P.L.C.

[57] ABSTRACT

Taste modifier comprising a flavone derivative as an active ingredient of the general formula (I):

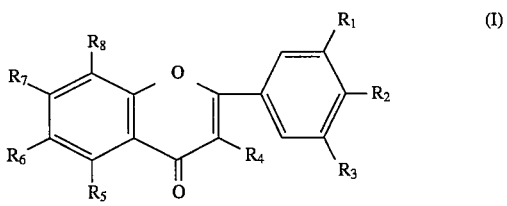

wherein $R_1$, $R_3$, $R_4$, $R_6$ and $R_8$ are independently a methoxy group or an hydrogen atom, $R_2$ and $R_7$ are methoxy groups, and $R_5$ is a methoxy group or an hydroxy group, and a method of modifying taste, comprising adding a taste-modifying effective amount of the flavone derivative (I) to a product used in a mouth or an orally ingestible product. Various factors associated with taste can be modified, for example, the derivative can enhance sourness, reduce saltiness, inhibit unpleasant lasting of sweetness, enhance refreshing flavor and its continuity, reduce flavor associated with acetic acid, and enhance body, deliciousness and savor associated with the combination of these tastes.

20 Claims, No Drawings

TASTE MODIFIER AND A METHOD OF MODIFYING TASTE

This application is a continuation of application Ser. No. 08/137,471, filed Oct. 18, 1993, now abandoned.

BACKGROUND OF THE INVENTION

1. Field of the Invention

The present invention relates to a taste modifier and a method of modifying taste. More particularly, the present invention relates to a taste modifier comprising a flavone derivative as an active ingredient, and a method of modifying taste which comprises adding an effective amount of the taste modifier to products used in a mouth or orally ingestible products.

2. Description of the Related Art

In general, flavones are known as substances having bitter taste.

Various efforts have been made for modifying sourness, saltiness, sweetness and flavor, or body, deliciousness or savor associated with the combination thereof in products, such as foods, cosmetics, drugs or quasi drugs.

For example, Japanese Unexamined Patent Publication No. 58-138363 (1983) discloses a method that wherein an amino acid, such as proline, aspartic acid and glutamic acid, is added to citrus fruit drinks containing a dibasic or tribasic acid for modifying the sourness. However, problems remain with the addition amino acid in that unpleasant aftertaste remains; the color of products is changed from yellow to brown by browning reaction in the presence of glucose, fructose or other reducing sugars; and unpleasant smells are present with elapsing time.

As for modifying saltiness, Japanese Unexamined Patent Publication No. 50-13568 (1975) discloses that a sweetner such as glycyrrhizin and dihydrochalcone can be added when processing foods. Also, a method of modifying saltiness by adding a seasoning, such as glycine and sodium L-glutamate, has been proposed.

In order to modify the sweetness, a method of changing the type of sugar used a method of adding a high magnification sweetener, such as Stevia extract and Aspartame (trade name), and a method of adding sugar alcohol, such as xylitol, have been proposed. However, such methods have drawbacks of causing the browning reaction and significant changes in physical and chemical properties, such as gravity and osmotic pressure. As a result, these methods can be used only in limited conditions.

Conventionally, a seasoning or fruit juice is added for enhancing the savor of foods. However, such addition of fruit juice is disadvantageous because it causes a person to taste or smell the seasoning or fruit juice as strange taste or smell.

In order to enhance the flavor, for example, to provide a refreshing flavor, menthol or menthol-containing essential oil, such as Japanese mint oil, and peppermint essential oil is added to chewing gum or refreshing drinks. However, the addition of such menthol or menthol-containing essential oil has a problem that bitter taste or stimulative smell is enhanced when the added amount is increased to enhance the refreshing flavor.

Alternatively, acetic acid or an acetic acid-containing fermented product is added to foods, cosmetics, drugs or quasi drugs for adding the sourness or modifying a storage property. However, when acetic acid or an acetic acid-containing fermented product is used for these purposes, the stimulative smell associated with acetic acid is adversely enhanced in accordance with the increase of added amount. Further, since some natural extracts such as karaya gum originally contain acetic acid, the smell of acetic acid associated with the use of such extracts gives an unpleasant effect on quality of taste.

The inventors of the present invention have studied for modification of the quality of taste by modifying various tastes contained in products used in a mouth or orally ingestible products, and have found that a flavone derivative, which is conventionally known as a compound having a bitter taste and included in fruit, rind or leaf of citrus fruits, are effective for modifying various tastes, thereby achieving the present invention.

SUMMARY OF THE INVENTION

The present invention provides a taste modifier comprising a flavone derivative as an active ingredient of the general formula (I):

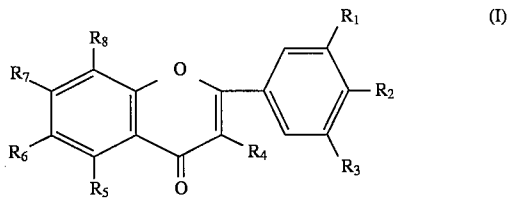

wherein $R_1$, $R_3$, $R_4$, $R_6$ and $R_8$ independently are methoxy group or hydrogen atom, $R_2$ and $R_7$ are methoxy group, and $R_5$ is methoxy group or hydroxy group, and a method of modifying taste comprising adding a taste-modifying effective amount of the flavone derivative (I) to a product used in a mouth or an orally ingestible product.

DETAILED DESCRIPTION OF THE INVENTION

The term of "taste modifying" of the present invention broadly means to modify various factors which concern taste. More particularly, it means that sourness, saltiness or sweetness and flavor, and body, deliciousness and savor associated with the combination thereof are enhanced or reduced to sense the original taste more pleasant in a mouth.

The mechanism of action of the flavone derivative (I) that is the active ingredient of the present invention has not been made clear yet. However, for example, the mechanism for modifying the saltiness associated with salt or the flavor (stimulative smell associated with acetic acid) of vinegar seems to be achieved by masking.

More particularly, as for the sourness associated with edible acids, for example organic acids such as citric acid and ascorbic acid, phosphoric acid and phytic acid, the flavone derivative (I) of the present invention acts on enhancing the sourness without decreasing pH of products, or on reducing the sourness which may be sensed as monotonous.

As for the saltiness associated with substances having saltiness, for example, salts such as table salt, the flavone derivative (I) of the present invention acts on reducing the saltiness and on inhibiting brackish sensed as aftertaste of the saltiness.

The flavone derivative (I) of the present invention acts on inhibiting unpleasant lasting of the sweetness associated with substances having sweetness, for example, sugars such as glucose, maltose, sucrose, fructose and lactose or reducing sugar thereof; high magnification sweetner, such as Stevia extract and Aspartame; or amino acids having sweetness such as glycine and alanine.

As for the refreshing flavor associated with menthol, peppermint or mint, the flavone derivative (I) of the present invention acts on enhancing the refreshing flavor and on modifying the continuity of the flavor. Accordingly, the refreshing feeling associated with the refreshing flavor is also enhanced and the continuity of such feeling is modified.

As for the flavor (stimulated smell associated with acetic acid) associated with acetic acid or vinegar, the flavone derivative (I) of the present invention acts on reducing the flavor without affecting acidity and preservation effect of acetic acid, and changing physical property of the products.

As for the body, deliciousness and savor associated with the combination of the above sourness, saltiness, sweetness and flavor, the flavone derivative (I) of the present invention acts on reducing unpleasant characteristics by moderating the taste or smell and on enhancing the body, deliciousness and savor originally contained in the products without damaging them.

The terminology "products used in a mouth", means non-toxic products in the form of solid, liquid or semi-solid which are used in a mouth and taken out after it is used. Those taken orally, in part, are also included in the products used in a mouth.

Examples of the products used in a mouth include: cosmetics, drugs or quasi drugs, such as toothpaste, medical toothpaste, mouthwash, refreshing agent used in a mouth, gargle and buccal tablet.

The terminology, "orally ingestible products", means non-toxic products which can be taken orally in the form of solid, liquid or semi-solid products. For example, those taken out from the mouth, in part, such as chewing gum are also included in the orally ingestible products.

Examples of orally ingestible products include: Japanese style confections, such as rice cracker, cracknel of rice, pressure processing rice, bun with a bean-jam filling and candy; western style confections, such as cookie, biscuit, cracker, pie, sponge cake, castella, doughnut, waffle, pudding, butter cream, custard cream, cream puff, chocolate, chocolate confections, caramel candy, chewing gum, jelly, pancake and bread; snacks, such as potato chips and the like; iced sweets, such as ice cream, ice candy and sherbet; pastes, such as flour paste, peanut paste and fruits paste; pickles; processing meat such as ham, sausage, bacon, dry sausage and beef jerky; processing fish, such as ham made of fish meat, sausage made of fish meat, boiled fish paste, kind of fish paste, cake of pounded fish and Japanese deeply fried food; curries, such as instant curry, retort curry and tin curry; seasonings, such as miso, powdery miso, soy sauce, powdery soy sauce, unrefined soy sauce, sauce made of fish protein, sauce, ketchup, mayonnaise, solid bouillon cube, roast meat sauce, curry roux, stew base, soup base and broth base; milk products, such as yogurt and lactic acid drink containing lactic acid bacterium; drugs, or quasi drugs such as troche, drinkable preparations, granules or powders and tablets.

Next, the flavone derivative (I) of the present invention is described in detail.

As the flavone derivative (I), it is preferable that $R_5$ is a hydroxyl group and that $R_1$ to $R_8$ have 4 to 7 methoxy groups, in total. Larger numbers of methoxy groups are preferable. Particularly, it is preferred that each of $R_1$, $R_2$, $R_4$, $R_5$, $R_6$, $R_7$ and $R_8$ are a methoxy group, and $R_3$ is a hydrogen atom.

The flavone derivative (I) can be obtained by extracting, purifying and separating from natural products. Alternatively, a flavone derivative (I) obtained from natural products may be partially demethylated or methylated to form another flavone derivative (I) of the present invention.

Materials containing the flavone derivative (I) may include fresh or dry product of fruit, rind or leaf of the plant belonging to Rutaceae. These materials can be used as is, or by grinding or compressing.

The flavone derivative (I) may be obtained by extracting, purifying and separating such materials in accordance with the method described in Journal of Japanese Agricultural Chemical Society vol. 62, p. 1777 (1988), as follows.

First, the materials are extracted by heating with an organic solvent, such as ethanol, methanol or chloroform, followed by removing the organic solvent under reduced pressure to give an extract of the flavone derivatives (I). The extraction is preferably conducted one to several times for 1 to 10 hours. Next, water is added to the obtained extract and it is further extracted with ether. Subsequently, the dissolved portion, in ether, is subjected to column chromatography, such as silica gel column chromatography, thereby purifying the extract of the flavone derivatives (I).

In place of the solvent for the extraction listed above, supercritical fluid solvent, such as carbon dioxide and propane, or subcritical fluid solvent, such as carbon dioxide and propane can be used. Alternatively, if necessary, water, ethanol or the like may be used together with the above solvent as an entrainer.

The extract of the flavone derivatives (I) obtained by the processes described above is a mixture of the flavone derivatives (I) and may include a lot of impurities derived from materials, for example, hydrocarbons, such as limonene, linalool, geraniol, nerol, α-terpineol and citral; carbonyls; esters; alcohols; other perfumes; and carotenoid dyes, such as kryptoxanthine. The obtained extracts can be used as is for juices and the like as a colorant or material of perfumes of citrus fruits. Such usages are also included in the present invention.

However, when the extract of the flavone derivatives (I) contains various impurities derived from materials as described above, such impurities cause unpleasant smell or taste, or cause, coloring in products. Accordingly, in case that the extract is used other than for the colorant or perfume material of citrus fruits, it is necessary to provide a purifying process after extracting, followed by removing the solvent in order to eliminate the impurities.

In addition to the column chromatography using silica gel, examples of the purifying process include: column chromatography using aluminum oxide, alkylsilyl silica gel, arylsilyl silica gel or the like; liquid-liquid partition chromatography using hexane, pentane or the like with water-containing methanol, water-containing ethanol or the like; liquid-liquid counter-current extraction using hexane, pentane or the like with water-containing methanol, water-containing ethanol or the like; or centrifugal partition chromatography. The extract may be purified by the combination of 2 or more these processes.

In the present invention, the purified extraction of the flavone derivatives (I) as a mixture of the flavone derivatives (I) may be used as an active ingredient. Alternatively, the mixture can be separated into each ingredient and one of the separated ingredient or the combination thereof may be used as an active ingredient.

Preparative high velocity liquid chromatography may be used for separating the flavone derivatives (I) into each ingredient.

The taste modifier of the present invention is comprised of one or more flavone derivatives (I) as an active ingredient, an excipient such as starch and lactose, and other additives such as preservatives may be further included therein.

The extract of the flavone derivatives (I) or the separated single ingredient or mixture thereof may be used per se or in the form of powder. They are powdered by a known method in the art. Alternatively, they may be used by dissolving in a solvent such as ethanol, glycerin and propylene glycol. Further, in case that the product used in a mouth or orally ingestible product is oily, acceptable oil products such as vegetable oil may be added thereto.

A method of modifying taste of the present invention comprises adding a taste-modifying effective amount of the flavone derivative (I) to a product used in a mouth or orally ingestible product as an active ingredient. In the case of using mixture of two or more flavone derivatives (I) as an active ingredient, the taste-modifying effective amount of the mixture is added.

The taste-modifying effective amount mentioned above indicates the amount with which the taste of products used in a mouth or orally ingestible product can be modified. The taste-modifying effective amount is suitably determined depending on the type of product, and a content of the substance to be modified, for example those having edible acid, menthol, peppermint, mint, acetic acid, vinegar, salts and substances having sweetness. Preferably, the taste-modifying effective amount is 0.1 ppb to 1 ppm, more preferably 1 ppb to 0.1 ppm. When flavones are added in this type of concentration, they do not cause a bitter taste by themselves.

In the case of applying the taste modifier to solid products, it is preferable to add the taste modifier in the form of powder. For applying to semi-solid or liquid products, it is preferably added in the form of liquid by dissolving the taste modifier into the above-mentioned solvent.

EXAMPLE

The present invention is further illustrated with respect to the following examples, but it is not intended to limit the scope of the invention thereto.

Extraction Example 1

In accordance with a method described in Journal of Japanese Agricultural Chemical Society, vol. 62, p.1777 (1988), 5 kg of rind of commercially available Iyokan (Japanese citrus) was refluxed to extract with 20 liters of ethanol, followed by removing the ethanol under reduced pressure to obtain an extract of the flavone derivatives (I). Then, after adding water, the extract of the flavone derivatives (I) was extracted with ether, and the solution of ether was subjected to silica gel column chromatography, thereby purifying the extract of the flavone derivatives (I). Next, the purified extract was subjected to preparative high velocity liquid chromatography under the condition described below to separate the following compounds 1 to 8.

Type: Pump 887-PU, made by NIHON BUNKO KABUSHIKI KAISHA

Detector: 870-UV, UV/visible light detector

Measured wavelength: 310 nm

Column: DEVEROSIL-ODS-5, made by NOMURA KAGAKU KABUSHIKI KAISHA, inner diameter 20 mm, length 250 mm Mobile phase: Acetonitrile/water=6/4 (v/v)

Flow rate: 3.0 ml/min.

The structures of the obtained compounds 1 to 8 were characterized by Mass Spectrum (hereinafter referred to MS) and Proton Nuclear Magnetic Resonance Spectrum (hereinafter referred to 1H-NMR). As for the Mass Spectrum, M-80 made by Hitachi Seisakusho was used with 20 eV of voltage for acceleration and the data were measured by the direct introduction method. As for the Proton Nuclear Magnetic Resonance Spectrum, XL-300 made by Valian Instruments was used with a magnetic field of 300 MHz and the data was measured by using chloroform as a solvent and tetramethylsilane as an internal standard. The spectrum data are indicated by $\delta$:ppm and the coupling constant is indicated by J:Hz. The letters s, d and dd indicate singlet, doublet and double doublet, respectively.

The melting point, Mass Spectrum and Proton Nuclear Magnetic Resonance Spectrum of the obtained compounds 1 to 8 were measured. The results and name of the compounds are listed as follows:

Compound 1: 3',4',5,6 7-pentamethoxyflavone
  Melting point 180° C.
  MS m/z 372 (M+)
  1H-NMR $\delta$3.92 (3H,s), 3.96 (3H,s), 3.98 (3H,s), 4.00 (6H,S) , 6.66 (1H,s), 6.88 (1H,s), 6.97 (1H,d,J=8 ), 7.33 (1H, d,J=2), 7.51 (1H,dd,J=2,8 ).

Compound 2: 3',4', 5,6,7,8-hexamethoxyflavone
  Melting point 134°–135° C.
  MS m/z 402 (M+)
  1H-NMR $\delta$3.96 (6H,s), 3.97 (3H,s), 3.98 (3H,s),4.03 (3H,s), 4.11 (3H,s), 6.62 (1H,s), 7.00 (1H,d,J=8), 7.41 (1H, d,J=2), 7.57 (1H,dd,J=2,8).

Compound 3: 4',5,6,7,8-pentamethoxyflavone
  Melting point 153°–154.5° C.
  MS m/z 372 (M+)
  1H-NMR $\delta$3.89 (3H,s), 3.95 (6H,s), 4.02 (3H,s), 4.10 (3H,s), 6.60 (1H,s), 7.03 (2H,d,J=9), 7.88 (2H,d,J=9).

Compound 4: 3',4',5,7,8-pentamethoxyflavone
  Melting point 196° C.
  MS m/z 372 (M+)
  1H-NMR $\delta$3.96 (6H,s), 3.98 (3H,s), 4.00 (3H,s), 4.01 (3H,s), 6.62 (1H,s), 6.44 (1H,s), 6.99 (1H,d,J=8), 7.42 (1H,d,J=2), 7.59 (1H,dd,J=2,8).

Compound 5: 3',4', 5,7-tetramethoxyflavone
  Melting point 198° C.
  MS m/z 342 (M+)
  1H-NMR $\delta$3.93 (3H,s), 3.96 (3H,s), 3.97 (3H,s), 3.98 (3H,s), 6.39 (1H,d,J=2), 6.57 (1H,d,J=2), 6.62 (1H,s), 6.97 (1H,d,J=8), 7.33 (1H,d,J=2), 7.52 (1H,dd,J=2,8).

Compound 6: 5,7,8,4'-tetramethoxyflavone
  Melting point 217° C.
  MS m/z 342 (M+)
  1H-NMR $\delta$3.89 (3H,s), 3.96 (3H,s), 3.99 (3H,s), 4.00 (3H,s), 6.44 (1H,s), 6.61 (1H,s), 7.02 (2H,d,J=9), 7.89 (2H, d,J=9).

Compound 7: 3,3',4',5,7,8-hexamethoxyflavone
  Melting point 174° C.
  MS m/z 402 (M+)
  1H-NMR $\delta$3.90 (3H,s), 3.94 (3H,s), 3.97 (6H,s), 4.00 (3H,s), 6.42 (1H,s), 7.01 (1H,d,J=8), 7.84 (1H,d,J=2), 7.86 (1H,dd,J=2,8).

Compound 8: 4',5,7-trimethoxyflavone
  Melting point 158° C.
  MS m/z 312 (M+)
  1H-NMR $\delta$3.89 (3H,s), 3.92 (3H,s), 3.96 (3H,s), 6.38 (1H,d,J=2), 6.56 (1H,d,J=2), 6.60 (1H,s), 7.00 (2H,d,J=9), 7.83 (1H,d,J=9).

(Extraction Example 2

In accordance with a method described in Chem. Pharm. Bull., Vol. 35, p. 3025 (1987), 1 kg of dried rind of Citrus Depressa was refluxed to extract with 10 liters of methanol, followed by removing the methanol under reduced pressure to obtain an extract of the flavone derivatives (I). Then, water and ethyl acetate were added to the extract to obtain an ethyl acetate layer. Ethyl acetate was removed under reduced pressure. Next, after adding benzene, the residue was subjected to silica gel column chromatography to purify the extract of the flavone derivatives (I). The purified extract was subjected to preparative high velocity liquid chromatography, thereby separating the following compounds 9 and 10.

The structures of the obtained compounds 9 and 10 were characterized in the same manner described in Extraction Example 1. The results and name of the compounds are listed as follows:

Compound 9: 5-hydroxy-4',6,7,8-tetramethoxyflavone
  Melting point 175° C.
  MS m/z 358 (M+)
  1H-NMR δ3.90 (3H,s), 3.96 (6H,s), 4.08 (3H,s), 6.56 (1H,s), 7.01 (2H,d,J=9), 7.92 (2H,d,J=9).

Compound 10: 5-hydroxy-3',4',6,7,8-pentamethoxyflavone
  Melting point 144° C.
  MS m/z 388 (M+)
  1H-NMR δ3.92 (12H,s), 4.02 (3H,s), 6.46 (1H,s), 6.90 (1H,d,J=9), 7.32 (1H,d,J=2), 7.51 (1H,dd,J=9,2).

Extraction Example 3

In accordance with a method described in Chem. Pharm. Bull., Vol. 37, p. 358 (1989), 1 kg of dried leaves of Murraya Paniculata was extracted with chloroform at room temperature, followed by removing the chloroform under reduced pressure to obtain an extract of the flavone derivative (I). Then, after adding benzene, the extract of the flavone derivatives (I) was subjected to silica gel column chromatography and eluted with benzene/acetone solvent, while the composition rate v/v is being changed to increase the content of acetone gradually from 9/1 to 7/1, 4/1 and 3/1. The flavone derivatives (I) were found in benzene/acetone fraction of 7/1 (v/v). The fraction containing the flavone derivatives (I) was subjected to silica gel column chromatography again and eluted with benzene/acetone (8/1 (v/v)) solvent, thereby purifying the extract of the flavone derivatives (I). The purified extract was subjected to preparative high velocity liquid chromatography, thereby separating the following compound 11.

The structure of the obtained compound 11 was characterized in the same manner described in Extraction Example 1. The result and name of the compound are listed as follows:

Compound 11: 3,3',4',5,5',6,7,8-octamethoxyflavone
  Melting point 125°–127° C.
  MS m/z 468 (M+)
  1H-NMR δ3.8–4.1 (24H), 7.52 (2H,s).

Extraction Example 4

Under reduced pressure of 20 mmHg, 1000 g of tangerine oil (corresponding to the extract of the flavone derivative (I)) contained in the rind of the plant belonging to Rutaceae was condensed to obtain 200 g of condensed product. A column having 200 mm in inner diameter and 1000 mm in length was filled with 6000 g of silica gel having a particle diameter of 150–425 μm that is dispersed in benzene, and condensed tangerine oil was applied thereto. Next, 12 liters of benzene was flowed for 2 hours thereto to remove the fraction eluted with benzene. Then, 36 liters of 40% (v/v) ethyl acetate in benzene was flowed for 6 hours to obtain a fraction containing the flavone derivatives (I). The obtained fraction containing the flavone derivatives (I) was condensed and was subjected to chromatography under the same condition again, thereby obtaining 20 g of white solid (hereinafter referred to Extract 1) as a purified extract of the flavone derivatives (I) without smell and color associated with the raw material.

Example 1

Enhancing the sourness

Compounds 1 to 11 of the flavone derivative (I) were used as a taste modifier to prepare acid sugar solution having compositions as follows:

| | |
|---|---|
| Granulated sugar | 50 (g) |
| Fructose/Glucose sugar solution | 80 (g) |
| Citric acid (crystal) | 1.000 (g) |
| L-ascorbic acid | 0.200 (g) |
| Flavone derivative (I) | 0.00001 (g) |
| Water | 869 (g) |

As a control, 21 types of acid sugar solutions are used. In the control, the flavone derivative (I) is removed from the above composition and the content of citric acid is varied from 1,000 g to 1.500 g by 0.025 g.

Sensory tests were carried out by 8 trained panellers in accordance with a limiting method described in the Hand Book of Sensory evaluation, edited by Research Committee of sensory evaluation, Union of Japanese Scientists and Engineers, p.398 (1973) in use of acid sugar solutions containing respective flavone derivatives (I) and another acid sugar solutions having a various content of citric acid.

As for the content of citric acid, two types of sensory tests were conducted, one was an ascending system (testing from solution with low concentration) and another was a descending system (testing from solution with high concentration).

The sensory evaluation was made by a value of enhancing the sourness. The value of enhancing the sourness was calculated by the following formula based on the content of citric acid in acid sugar solutions with varied concentration of citric acid, which has an equivalent stimulation with an acid sugar solution containing the flavone derivative (I).

Value of enhancing the sourness=(content of citric acid in acid sugar solution sensed as an equivalent stimulation/content of citric acid in acid sugar solution containing the flavone derivative (I))×100

The results are shown in Table 1.

TABLE 1

| | Sourness enhanced by the flavone derivative (I) | |
|---|---|---|
| | Value of enhancing the sourness | |
| Flavone derivative (I) | Ascending system | Descending system |
| Compound 1 | 119 | 121 |
| Compound 2 | 118 | 123 |
| Compound 3 | 120 | 123 |
| Compound 4 | 117 | 119 |
| Compound 5 | 118 | 121 |
| Compound 6 | 120 | 123 |
| Compound 7 | 116 | 119 |
| Compound 8 | 118 | 120 |
| Compound 9 | 117 | 119 |
| Compound 10 | 120 | 123 |
| Compound 11 | 125 | 128 |

As seen from the results, every flavone derivative (I) of the compounds 1 to 11 clearly enhanced the sourness of acid sugar solution.

Example 2

Enhancing the sourness (refreshing drink)

Compound 4 of the flavone derivative (I) was used as a taste modifier. Raw materials described below were mixed and stirred to dissolve. The solution was heated up to 93° C., immediately transmitted to a bottle and sealed. Then, it was cooled in water, thereby preparing refreshing drinks having the compositions as follows. A control was prepared by eliminating the compound 4 from the raw materials.

Sensory tests of the obtained refreshing drinks were carried out by 8 panellers.

As a result, the refreshing drink containing the flavone derivative (I) showed the taste of fruit juice and the sourness stronger than the control, and the quality of taste is significantly improved.

| | |
|---|---|
| Fructose/glucose sugar solution | 110 (g) |
| Citric acid (crystal) | 2 (g) |
| Lemon flavor | 2 (g) |
| Flavone derivative (I) (Compound 4) | 0.0002 (g) |
| Water | 885 (g) |

Example 3

Enhancing the sourness (jelly)

Extract 1 of the flavone derivative (I) was used as a taste modifier. Raw materials listed below except for flavor were mixed and heated to dissolve. The solution was sterilized at 80° C. for 10 minutes, and then the flavor was added thereto. Next, it is filled into a vessel and cooled, thereby preparing strawberry jelly. A control was prepared by eliminating Extract 1 from the raw materials.

Sensory tests for obtained strawberry jelly were carried out by 8 panellers.

As a result, the flavone derivative (I)-containing strawberry jelly showed the taste of fruit juice and sourness stronger than the control, and the quality of taste is significantly improved.

| | |
|---|---|
| Granulated sugar | 50.0 (g) |
| Fructose/glucose sugar solution | 132.0 (g) |
| Gelation agent | 10.0 (g) |
| Citric acid (crystal) | 2.0 (g) |
| Flavor | 2.0 (g) |
| Red cabbage colorant | 1.0 (g) |
| Extract 1 | 0.0001 (g) |
| Water | 803.0 (g) |

Example 4

Enhancing the refreshness associated with the refreshing flavor and its continuity, and improving the quality of taste (chewing gum).

| | Flavor composition A | Flavor composition B |
|---|---|---|
| Peppermint essential oil | 70 (w/w)% | 70 (w/w)% |
| Menthol | 30 (w/w)% | 30 (w/w)% |
| Flavone derivative (I) | — | 0.0002 (w/w)% |

Extract 1 of the flavone derivatives (I) was used as a taste modifier. Chewing gum containing the above flavor composition A (control) or B (containing the flavone derivative (I)) was prepared.

First, 25 g of gum base, 20 g of sugar, 52 g of water-containing glucose and 3 g of thick malt syrup were mixed while heating, and then the above flavor composition A was added thereto such that 1 (w/w) % of the flavor composition was contained and mixed, thereby preparing flavone derivative (I) free chewing gum.

In accordance with the same method, flavone derivative (I)-containing chewing gum was prepared by using the flavor composition B in stead of the flavor composition A.

Sensory tests for obtained chewing gum were carried out by 8 panellers comprised of 6 males and 2 females at the age from 20 to 40.

The results are shown in Table 2.

TABLE 2

| | Sensory Test Results (number of people) | |
|---|---|---|
| Test items | Those who sensed B additive is better | Those who sensed no difference |
| Refreshness | 7 | 1 |
| Continuity of the refreshness | 8 | 0 |
| Quality of taste | 8 | 0 |

As seen from Table 2, the flavone derivative (I)-containing chewing gum showed strong refreshness associated with the refreshing flavor and continuity of the refreshness greater than that of the flavone derivative (I) free. Also, the quality of taste of the chewing gum was surely improved by adding the flavone derivative (I).

Therefore, it is clear that the flavone derivative (I) has enhancing effect of the refreshing flavor and continuing effect thereof.

Example 5

Enhancing the refreshness associated with the refreshing flavor and its continuity, and improving the quality of taste (hard candy)

| | Flavor composition C | Flavor composition D |
|---|---|---|
| Menthol | 40 (g) | 40 (g) |
| Peppermint essential oil | 20 (g) | 20 (g) |
| Mint essential oil | 20 (g) | 20 (g) |
| Eucalyptus essential oil | 10 (g) | 10 (g) |
| Spearmint essential oil | 7 (g) | 7 (g) |
| Wintergreen essential oil | 3 (g) | 3 (g) |
| Flavone derivative (I) | — | 0.0001 (g) |

Compound 1 of the flavone derivative (I) was used as a taste modifier. Hard candy containing the above flavor composition C (control) or D (containing the flavone derivative (I)) was prepared.

First, 60 g of sugar, 40 g of thin malt syrup and 20 g of water were mixed and heated up to about 150° C. to boil down, and then allowed to cool to about 120° C. while stirring. Next, the above flavor composition C was added thereto such that 0.1 (w/w) % of the flavor composition was contained and it is poured into a box, thereby preparing flavone derivative (I) free hard candy.

Alternatively, the flavor composition D was used in instead of the flavor composition C to prepare flavone derivative (I)-containing hard candy in accordance with the same method.

Sensory tests for obtained hard candy were carried out by 8 panellers comprised of 6 males and 2 females at the age from 20 to 40.

The results are shown in Table 3.

TABLE 3

| | Sensory Test Results (number of people) | |
|---|---|---|
| Test items | Those who sensed D additive is better | Those who sensed no difference |
| Refreshness | 7 | 1 |
| Continuity of the refreshness | 8 | 0 |
| Quality of taste | 6 | 2 |

As seen from Table 3, the flavone derivative (I)-containing hard candy showed strong refreshness associated with the refreshing flavor and continuity of the refreshness greater than that of the flavone derivative (I) free. Also, the quality of taste of the hard candy was improved by adding the flavone derivative (I).

Therefore, it is clear that the flavone derivative (I) has enhancing effect of the refreshing flavor and continuing effect thereof.

Example 6

Enhancing the refreshness associated with the refreshing flavor and its continuity, and improving the quality of taste (mouth refreshing agent)

| | Flavor composition E | Flavor composition F |
|---|---|---|
| Menthol | 30 (g) | 30 (g) |
| Wintergreen essential oil | 20 (g) | 20 (g) |
| Peppermint essential oil | 20 (g) | 20 (g) |
| Spearmint essential oil | 10 (g) | 10 (g) |
| Eucalyptus essential oil | 5 (g) | 5 (g) |
| Anise essential oil | 3 (g) | 3 (g) |
| Ethanol | 12 (g) | 12 (g) |
| Flavone derivative (I) | — | 0.00005 (g) |

Compound 9 of the flavone derivative (I) was used as a taste modifier. Mouth refreshing agent comprising the above flavor composition E (control) or F (containing the flavone derivative (I)) was prepared.

First, 30 g of ethanol, 10 g of glycerin, 2 g of polyoxyethylene hardened castor oil, 0.1 g of sodium saccharin, 0.005 g of chlorhexidine and 58 g of water were mixed, and the above flavor composition E was added thereto such that 0.1 (w/w) % of the flavor composition was contained, thereby preparing flavone derivative (I) free mouth refreshing agent. Alternatively, the flavor composition F was used instead of the flavor composition E to prepare flavone derivative (I)-containing mouth refreshing agent.

Sensory tests for obtained mouth refreshing agents were carried out by 8 panellers comprised of 6 males and 2 females at the age from 20 to 40.

The results are shown in Table 4.

TABLE 4

| | Sensory Test Results (number of people) | |
|---|---|---|
| Test items | Those who sensed F additive is better | Those who sensed no difference |
| Refreshness | 7 | 1 |
| Continuity of the refreshness | 8 | 0 |
| Quality of taste | 6 | 2 |

As seen from Table 4, the flavone derivative (I) containing mouth refreshing agent had strong refreshness associated with the refreshing flavor and continuity of the refreshness greater than that of the flavone derivative (I) free agent. Also, the quality of taste of the mouth refreshing agent was clearly improved by adding the flavone derivative (I).

Therefore, it is clear that the flavone derivative (I) has enhancing effect of the refreshing flavor and continuity effect thereof.

Example 7

Enhancing the refreshness associated with the refreshing flavor and its continuity, and improving the quality of taste (refreshing drink)

| | Flavor composition G | Flavor composition H |
|---|---|---|
| Isoamyl acetate | 1 (g) | 1 (g) |
| Ethyl acetate | 0.5 (g) | 0.5 (g) |
| Peppermint essential oil | 0.2 (g) | 0.2 (g) |
| Menthol | 0.1 (g) | 0.1 (g) |
| Ethanol | 56.2 (g) | 56.2 (g) |
| Flavone derivative (I) | — | 0.000001 (g) |
| Water | 42 (g) | 42 (g) |

Compound 11 of the flavone derivative (I) was used as a taste modifier. Refreshing drink containing the above flavor composition G (control) or H (containing the flavone derivative (I)) was prepared.

First, 10 g of fructose/glucose sugar solution, 0.1 g of citric acid (crystal), 0.2 g of the flavor composition G and 88.5 g of water were mixed to dissolve, followed by heating up to 93° C., immediately transmitted to a bottle and sealed. Then, it was cooled in water, thereby preparing flavone derivative (I) free refreshing drink.

Alternatively, flavone derivative (I)-containing refreshing drink was prepared by the same method using the flavor composition H instead of the flavor composition G.

Sensory tests for obtained refreshing drink were carried out by 8 panellers comprised of 6 males and 2 females at the age from 20 to 40.

The results are shown in Table 5.

TABLE 5

| | Sensory Test Results (number of people) | |
|---|---|---|
| Test items | Those who sensed H additive is better | Those who sensed no difference |
| Refreshness | 7 | 1 |
| Continuity of the refreshness | 8 | 0 |
| Quality of taste | 6 | 2 |

As seen from Table 5, the flavone derivative (I)-containing refreshing drink had strong refreshness associated with the refreshing flavor and continuity of the refreshness greater than that of the flavone derivative (I) free refreshing drink. Also, the quality of taste of the refreshing drink was clearly improved by adding the flavone derivative (I).

Therefore, it is clear that the flavone derivative (I) has enhancing effect of the refreshing lavor and continuity effect thereof.

Example 8

Reducing flavor associated with acetic acid (stimulative smell associated with acetic acid)

Influence over the sourness of acetic acid or the flavor associated with acetic acid by addition of the taste modifier of the present invention was examined by sensory tests below.

Extract 1 of the flavone derivative (I) was used as a taste modifier. The taste modifier was added to acetic acid solution. Changes in the sourness and the flavor associated with acetic acid (hereinafter referred to stimulative smell) were examined by sensory tests.

The sensory tests were carried out by containing a sample in a mouth, and closing nasal cavity to examine the sourness or opening nasal cavity to examine the sourness and the stimulative smell. Changes in the stimulative smell were determined by the difference between sensory evaluation for the sourness and sensory evaluation for both of sourness and stimulative smell.

First, 0.07, 0.08, 0.09, 0.10, 0.11, 0.12, 0.13, 0.14, 0.15, 0.16, 0.17, 0.18, 0.19 and 0.20 w/v % acetic acid solutions were prepared as standard solutions by changing the hydrogen ion concentration. Degrees of sourness and sourness-stimulative smell were defined as 70, 80, 90, 100, 110, 120, 130, 140, 150, 160, 170, 180, 190 and 200 for the standard solutions, respectively.

Degrees of sourness and sourness-stimulative smell of samples were determined by choosing a standard solution having the same sourness or sourness-stimulative smell as that of each one of the sample solution.

The sensory tests were carried out by 20 panellers comprised of 10 males and 10 females. The results were collected and subjected to a verification by a pare test. The sourness and the sourness-stimulative smell which were significant at $p<0.05$ were judged to be the degree of sourness or sourness-stimulative smell of sample solutions. The difference between the degrees of sourness and sourness-stimulative smell was defined as the degree of changes in the stimulative smell.

The results are shown in Table 6.

TABLE 6

Sensory Test Results

| | Concentration of the flavone derivative (I) (ppb) | | | | |
|---|---|---|---|---|---|
| | 0 | 10 | 100 | 1000 | 10000 |
| Sourness degree | 100 | 100 | 110 | 110 | 120 |
| Sourness-stimulative smell degree | 100 | 90 | 90 | 80 | 80 |
| Degree of change in the stimulative smell | 0 | 10 | 20 | 30 | 40 |

As seen from Table 6, it is clear that the stimulative smell associated with acetic acid solution was reduced by addition of the flavone derivative (I).

Therefore, it is clear that the flavone derivative (I) has reducing effect of the flavor associated with acetic acid (stimulative smell associated with acetic acid).

Example 9

Reducing the flavor associated with acetic acid (stimulative smell associated with acetic acid (toothpaste)

| Sorbitol (70% solution) | 78 (g) |
|---|---|
| SYLOID244FP silica | 10 (g) |
| SYLOID63FP silica | 4 (g) |
| Water | 4 (g) |
| Sodium lauryl sulfate | 1 (g) |
| Flavor | 1 (g) |
| Karaya gum | 2 (g) |
| Sodium hydroxide (50% solution) | 0.2 (g) |
| Blue colorant No. 1 | 0.015 (g) |
| Sodium saccharine | 0.02 (g) |

Sorbitol was heated to 70° C., followed by adding sodium saccharine and silica slowly thereto and by stirring well. Then, water previously heated to 70° C., karaya gum, sodium lauryl sulfate and sodium hydroxide were added sequentially while stirring. Finally, flavor was added thereto to prepare toothpaste as a control. Alternatively, flavone derivative (I)-containing toothpaste was prepared by adding 0.0000001 part by weight of Compound 3 of the flavone derivative (I) to 1 part by weight of similarly prepared toothpaste.

Sensory tests for obtained toothpaste were conducted by 9 panellers comprised of 6 males and 3 females.

The results are shown in Tables 7 and 8.

TABLE 7

Sensory Test Results (number of people)

| Test item | Those who sensed the flavone derivative (I) additive is reduced | Those who sensed no difference |
|---|---|---|
| Stimulative smell | 8 | 1 |

TABLE 8

Sensory Test Results (number of people)

| Test item | Those who sensed difference exists | Those who sensed no difference |
|---|---|---|
| Viscosity | 0 | 9 |

As seen from Tables 7 and 8, there was no difference in viscosity, but the stimulative smell associated with acetic acid of the flavone derivative (I)-containing toothpaste was reduced from that of the flavone derivative (I) free.

Therefore, it is clear that the flavone derivative (I) acts on reducing the flavor associated with acetic acid (stimulative smell associated with acetic acid).

Example 10

Reducing the flavor associated with acetic acid (stimulative smell associated with acetic acid (mayonnaise)

| Water | 253.3 g |
|---|---|
| Sugar | 40 g |
| Sodium glutamate | 0.5 g |

|  |  |
|---|---|
| Carrageenan | 11 g |
| Raw vinegar | 100 g |
| Salt | 20 g |
| Yolk | 75 g |
| Corn salad oil | 500 g |

Compound 8 of the flavone derivative (I) was used as a taste modifier. First, sugar, sodium glutamate and carrageenan were dissolved in water, followed by adding raw vinegar, salt and yolk. Then, corn salad oil was added portionwise while stirring, and emulsified by the use of colloid mill, thereby preparing mayonnaise as a control. Alternatively, flavone derivative (I)-containing mayonnaise was prepared by adding 0.001 mg of Compound 8 to mayonnaise that was similarly prepared.

Sensory tests for obtained mayonnaise were conducted by 9 panellers comprised of 6 males and 3 females.

The results are shown in Table 9.

TABLE 9

Sensory Test Results (number of people)

| Test item | Those who sensed difference exists | Those who sensed no difference |
|---|---|---|
| Stimulative smell | 7 | 2 |

As seen from Table 9, it is clear that the stimulative smell associated with acetic acid was moderated by addition of the flavone derivative (I) to substance (mayonnaise) including acetic acid.

Therefore, it is clear that the flavone derivative (I) acts on reducing the flavor associated with acetic acid (stimulative smell associated with acetic acid).

Example 11

Modifying the saltiness

Extract 1 of the flavone derivative (I) was used as a taste modifier. First, 1 g, 3 g and 10 g of salt or sodium malate was added to 100 ml of water to prepare a standard solution. Alternatively, sample solutions were prepared by adding 1, 0.1, 0.01 ppm of Extract 1 to the standard solution, respectively.

Sensory tests were conducted by 5 trained panellers to examine saltiness modifying effect (so called saltiness adapting effect) and taste modifying effect.

It was evaluated by 5 points evaluation tests (5: significantly modified, 4: modified, 3: slightly modified, 2: no changes, and 1: deteriorated) and the average of the points of 5 panellers was calculated. Each sample solution was evaluated assuming that the standard solution has the point of 2.

The results are shown in Tables 10 and 11.

TABLE 10

| Saltiness Modifying Effect | | | | | | | | |
|---|---|---|---|---|---|---|---|---|
| Added amount of the flavone | Salt | | | | Sodium malate | | | |
| derivative (I) | 1% | 3% | 5% | 10% | 1% | 3% | 5% | 10% |
| 1.00 ppm | 3.6 | 4.0 | 3.4 | 3.4 | 3.0 | 3.0 | 2.6 | 2.6 |
| 0.10 ppm | 3.4 | 3.8 | 3.0 | 3.0 | 2.6 | 2.6 | 2.4 | 2.4 |
| 0.01 ppm | 2.4 | 3.8 | 2.6 | 2.6 | 2.6 | 2.6 | 2.2 | 2.2 |

TABLE 10-continued

| Saltiness Modifying Effect | | | | | | | | |
|---|---|---|---|---|---|---|---|---|
| Added amount of the flavone | Salt | | | | Sodium malate | | | |
| derivative (I) | 1% | 3% | 5% | 10% | 1% | 3% | 5% | 10% |
| Standard value | 2.0 | 2.0 | 2.0 | 2.0 | 2.0 | 2.0 | 2.0 | 2.0 |

TABLE 11

| Taste Modifying Effect | | | | | | | | |
|---|---|---|---|---|---|---|---|---|
| Added amount of the flavone | Salt | | | | Sodium malate | | | |
| derivative (I) | 1% | 3% | 5% | 10% | 1% | 3% | 5% | 10% |
| 1.00 ppm | 3.4 | 3.4 | 3.6 | 4.0 | 2.8 | 2.8 | 3.2 | 3.2 |
| 0.10 ppm | 3.0 | 3.0 | 3.4 | 3.8 | 2.6 | 2.6 | 2.8 | 3.2 |
| 0.01 ppm | 2.6 | 2.4 | 3.0 | 3.8 | 2.4 | 2.6 | 2.8 | 3.0 |
| Standard value | 2.0 | 2.0 | 2.0 | 2.0 | 2.0 | 2.0 | 2.0 | 2.0 |

As seen from Tables 10 and 11, it is clear that the saltiness and the taste of salt solution were modified by addition of the flavone derivative (I).

Therefore, it is clear that the flavone derivative (I) acts on modifying the saltiness (moderating the saltiness). Especially, in low salt concentration such as 1 to 3%, saltiness modifying effect (so called saltiness adapting effect) was exhibited significantly and in high salt concentration such as 5 to 10%, taste modifying effect (moderating the taste) was exhibited significantly.

Example 12

Modifying the saltiness

Compound 3 of the flavone derivative (I) was used as a taste modifier. First, 1 g, 3 g and 10 g of salt or sodium L-glutamate was added to 100 ml of water to prepare standard solutions. Alternatively, sample solutions were prepared by adding 1, 0.1, 0.01 ppm of Compound 3 to the standard solutions, respectively.

Sensory tests were conducted by 5 trained panellers to examine saltiness modifying effect (so called saltiness adapting effect) and brackish taste modifying effect.

Five points evaluation tests (5: significantly modified, 4: modified, 3: slightly modified, 2: no changes, and 1: deteriorated) were conducted and the average of the points of 5 panellers was calculated. Each sample solution was evaluated assuming that the standard solution has the point of 2.

The results are shown in Tables 12 and 13.

TABLE 12

| Saltiness Modifying Effect | | | | |
|---|---|---|---|---|
| Added amount of the flavone | Salt, sodium L-glutamate | | | |
| derivative (I) | 1% | 3% | 5% | 10% |
| 1.00 ppm | 4.4 | 4.0 | 4.0 | 3.8 |
| 0.10 ppm | 4.0 | 3.8 | 3.6 | 3.4 |

TABLE 12-continued

Saltiness Modifying Effect

| Added amount of the flavone derivative (I) | Salt, sodium L-glutamate | | | |
|---|---|---|---|---|
| | 1% | 3% | 5% | 10% |
| 0.01 ppm | 3.6 | 3.8 | 3.4 | 3.0 |
| Standard value | 2.0 | 2.0 | 2.0 | 2.0 |

TABLE 13

Brackish Taste Modifying Effect

| Added amount of the flavone derivative (I) | Salt | | | |
|---|---|---|---|---|
| | 1% | 3% | 5% | 10% |
| 1.00 ppm | 4.4 | 4.0 | 4.0 | 3.8 |
| 0.10 ppm | 4.0 | 3.8 | 3.6 | 3.4 |
| 0.01 ppm | 3.6 | 3.6 | 3.4 | 3.0 |
| Standard value | 2.0 | 2.0 | 2.0 | 2.0 |

As seen from Tables 12 and 13, it is clear that the saltiness and the brackish taste were modified by addition of the flavone derivative (I) to an aqueous solution containing salt and sodium L-glutamate.

Therefore, it is clear that the flavone derivative (I) acts on modifying the saltiness (moderating the saltiness) and the brackish taste (inhibiting the brackish taste) significantly.

Example 13

Modifying the saltiness (soy sauce with low salt concentration)

Compound 5 of the flavone derivative (I) was used as a taste modifier. To commercially available soy sauce with low salt concentration (salt concentration: 7 w/w %), 1, 0.1 and 0.01 ppm of the flavone derivative (I) was added respectively to prepare sample solutions. Sensory tests were carried out for the respective concentrations of sample solutions and ½ diluted solutions thereof. Flavone derivative (I) free solutions were used as standard solutions.

The sensory tests were conducted by 5 trained panellers to examine saltiness modifying effect (so called saltiness adapting effect) and brackish taste modifying effect.

Five points evaluation tests (5: significantly modified, 4: modified, 3: slightly modified, 2: no changes, and 1: deteriorated) were conducted and the average of the points of 5 panellers was calculated. Each sample solution was evaluated assuming that the standard solution has the point of 2.

The results are shown in Tables 14 and 15.

TABLE 14

Saltiness Modifying Effect

| Added amount of the flavone derivative (I) | Soy sauce | |
|---|---|---|
| | ½ dilution | Undiluted solution |
| 1.00 ppm | 4.4 | 4.0 |
| 0.10 ppm | 4.0 | 3.6 |
| 0.01 ppm | 3.8 | 3.6 |
| Standard value | 2.0 | 2.0 |

TABLE 15

Brackish Taste Modifying Effect

| Added amount of the flavone derivative (I) | Soy sauce | |
|---|---|---|
| | ½ dilution | Undiluted solution |
| 1.00 ppm | 4.0 | 4.0 |
| 0.10 ppm | 4.0 | 3.4 |
| 0.01 ppm | 3.6 | 3.4 |
| Standard value | 2.0 | 2.0 |

As seen from Tables 14 and 15, it is clear that the saltiness and the brackish taste were modified by addition of the flavone derivative (I) to soy sauce with low salt concentration.

Therefore, it is clear that the flavone derivative (I) acts on modifying the saltiness (moderating the saltiness) and the brackish taste (inhibiting the brackish taste) significantly.

Example 14

Modifying the saltiness and the savor (salted squid).

Compound 5 of the flavone derivative (I) was used as a taste modifier. To commercially available salted squids, 1, 0.1 and 0.01 ppm of the flavone derivative (I) was added respectively to prepare samples. Sensory tests were carried out for the saltiness and the savor of salted squid. Flavone derivative (I) free salted squids were used as standards.

The sensory tests were conducted by 5 trained panellers to examine saltiness modifying effect (so called saltiness adapting effect) and savor modifying effect.

Five points evaluation tests (5: significantly modified, 4: modified, 3: slightly modified, 2: no changes, and 1: deteriorated) were conducted and the average of the points of 5 panellers was calculated. Each sample solution was evaluated assuming that the standard solution has the point of 2.

The results are shown in Table 16.

TABLE 16

Saltiness and Savor Modifying Effect

| Added amount of the flavone derivative (I) | Salted squid | | |
|---|---|---|---|
| | Saltiness | Savor | Total evaluation |
| 1.00 ppm | 3.8 | 4.0 | 3.8 |
| 0.10 ppm | 3.4 | 3.8 | 3.6 |
| 0.01 ppm | 3.0 | 3.6 | 3.4 |
| Standard value | 2.0 | 2.0 | 2.0 |

As seen from Table 16, it is clear that the saltiness and the savor of salted squid were modified by addition of the flavone derivative (I).

Therefore, it is clear that the flavone derivative (I) acts on modifying the saltiness (moderating the saltiness) and the savor (enhancing the savor).

Example 15

Modifying the saltiness and the savor (ham made of pork loin).

Compound 6 of the flavone derivative (I) was used as a taste modifier. Ham made of pork loin was prepared by a general method, in use of pickle solutions containing the flavone derivative (I) in the amount of 1, 0.1 and 0.01 ppm and flavone derivative (I) free standard pickle solution, respectively. Sensory tests were carried out for modifying effects of the saltiness and the savor.

The sensory tests were conducted by 5 trained panellers to examine saltiness modifying effect (so called saltiness adapting effect) and savor modifying effect.

Five points evaluation tests (5: significantly modified, 4: modified, 3: slightly modified, 2: no changes, and 1: deteriorated) were conducted and the average of the points of 5 panellers was calculated. Each sample solution was evaluated assuming that the standard solution has the point of 2.

The results are shown in Table 17.

| Formulation of pickle solution | |
| --- | --- |
| Salt | 9.0 g |
| Calamine 10N (chromophoric agent) | 0.6 g |
| Sausage mix HS (pickling agent) | 3.0 g |
| Powder of the white of egg | 6.0 g |
| Sugar | 1.8 g |
| Sodium L-glutamate | 0.6 g |
| Flavone derivative (I) | 1.2 g |
| Iced water | 77.8 g |

<Method of preparing ham made of pork loin>

The pickle solution containing the above was prepared and cooled for a night. Then, raw meat (native pork) was molded and the pickle solution was injected at a rate of 20% to the molded meat. After injection, the molded meat was tumbled with tumbler (12 R. P. M./60 minutes) and salted for a night. It was packed in a container and subjected to dry heat at 60° C. for 60 minutes, smoke at 70° C. for 40 minutes and steam at 78° C. (the temperature of the center raised to 70° C.) to finish the processing. The processed meat was cooled for a night and evaluated.

TABLE 17

| | Saltiness and Savor Modifying Effect | | |
| --- | --- | --- | --- |
| Added amount of the flavone derivative (I) | Ham made of pork loin | | |
| | Saltiness | Savor | Total evaluation |
| 1.00 ppm | 3.4 | 3.4 | 3.4 |
| 0.10 ppm | 3.0 | 3.0 | 3.0 |
| Standard value | 2.0 | 2.0 | 2.0 |

As seen from Table 17, it is clear that the saltiness and the savor of ham made of pork loin were modified by addition of the flavone derivative (I).

Therefore, it is clear that the flavone derivative (I) acts on modifying the saltiness (moderating the saltiness) and the savor (enhancing the savor).

Example 16

Modifying the saltiness and the savor (toothpaste)

Compound 7 of the flavone derivative (I) was used as a taste modifier. To commercially available toothpaste (containing salt), the flavone derivative (I) was added in the amount of 1, 0.1 and 0.01 ppm respectively to prepare samples. Sensory tests were carried out for modifying effects of the saltiness and the savor of toothpaste. Flavone derivative (I) free toothpaste was used as a standard substance.

The sensory tests were conducted by 5 trained panellers to examine saltiness modifying effect (so called saltiness adapting effect) and savor modifying effect.

Five points evaluation tests (5: significantly modified, 4: modified, 3: slightly modified, 2: no changes, and 1: deteriorated) were conducted and the average of the points of 5 panellers was calculated. Each sample solution was evaluated assuming that the standard solution has the point of 2.

The results are shown in Table 18.

TABLE 18

| | Saltiness and Savor Modifying Effect | |
| --- | --- | --- |
| Added amount of the flavone derivative (I) | Toothpaste | |
| | Saltiness | Savor |
| 1.00 ppm | 3.4 | 3.0 |
| 0.10 ppm | 2.6 | 2.4 |
| 0.01 ppm | 2.2 | 2.2 |
| Standard value | 2.0 | 2.0 |

As seen from Table 18, it is clear that the saltiness and the savor of toothpaste (containing salt) were modified by addition of the flavone derivative (I).

Therefore, it is clear that the flavone derivative (I) acts on modifying the saltiness (moderating the saltiness) and the savor (enhancing the savor).

Example 17

Modifying the sweetness and the savor (soft drink)

| Fructose/glucose sugar solution | 100 g |
| --- | --- |
| Stevia extract | 0.4 g |
| Citric acid (crystal) | 1 g |
| Flavone derivative (I) | 0.0005 g |
| Flavor | 0.1 g |
| Water | 898 g |

Extract 1 of the flavone derivative (I) was used as a taste modifier. Raw materials listed above were mixed and stirred to dissolve, followed by heating up to 93° C. It was transmitted in a bottle immediately and sealed, and cooled, thereby preparing soft drink. Alternatively, flavone derivative (I) free soft drink was prepared as a control.

The sensory tests for obtained soft drink were conducted by 8 trained panellers comprised of 6 males and 2 females at the age from 20 to 40.

The results are shown in Table 19.

TABLE 19

| | Sensory Test Results (number of people) | |
| --- | --- | --- |
| Test items | Those who sensed the flavone derivative (I) additive is better | Those who sensed no difference |
| Quality of sweetness | 6 | 2 |
| Inhibiting effect of unpleasant lasting of sweetness | 8 | 0 |
| Quality of taste | 7 | 1 |

As seen from Table 19, it is clear that the quality of sweetness was modified and the lasting of sweetness of high magnification sweetner that gives unpleasant feeling was inhibited, thereby improving the quality of taste.

Therefore, it is clear that the flavone derivative (I) acts on modifying the sweetness.

Example 18

Modifying the sweetness and the savor (ice cream)

Compound 2 of the flavone derivative (I) was used as a taste modifier. Ice cream containing 5 w/w % of sugar, 12 w/w % of fructose condensed milk and 10 w/w % of thick malt syrup as sweetening agents was used as a control. The control and ice cream containing 0.00001 w/w % of the flavone derivative (I) were made by a general method. Sensory tests for the sweetness and the savor were conducted by 10 trained panellers comprised of 6 males and 4 females at the age from 20 to 40.

As a result, all the panellers sensed that the sweetness and the savor of the flavone derivative (I)-containing ice cream was better than that of the control.

Accordingly, it is clear that the sweetness and the savor of ice cream were modified and the quality of taste was improved by additional of the flavone derivative (I).

Therefore, it is clear that the flavone derivative (I) acts on modifying the sweetness (inhibiting the lasting of sweetness) and modifying the savor (enhancing the savor).

Example 19

Modifying the sweetness and the savor (sponge cake).

Compound 4 of the flavone derivative (I) was used as a taste modifier and 22 w/w % of white sugar was used as a sweetening agent. In accordance with a general method, sponge cake containing 0.0001 w/w % of the flavone derivative (I) and flavone derivative (I) free sponge cake were prepared. Sensory tests for the sweetness and the savor were conducted by 10 panellers comprised of 6 males and 4 females at the age from 20 to 40.

As a result, all the panellers sensed that the sweetness and the savor of the flavone derivative (I)- containing sponge cake was better than that of the control.

Accordingly, it is clear that the sweetness and the savor of sponge cake were modified and the quality of taste was improved by additional of the flavone derivative (I).

Therefore, it is clear that the flavone derivatives (I) acts on modifying the sweetness (inhibiting the lasting of sweetness) and modifying the savor (enhancing the flavor).

Example 20

Modifying the savor (boiled fish paste)

Compound 7 of the flavone derivative (I) was used as a taste modifier. In accordance with a general method, boiled fish paste containing 0.0001 w/w % of the flavone derivative (I) and flavone derivative (I) free boiled fish paste were prepared in use of 1.5 w/w % glycine. Sensory tests for the savor were conducted by 10 panellers comprised of 6 males and 4 females at the age from 20 to 40.

As a result, all the panellers sensed that the savor of the flavone derivative (I)-containing boiled fish paste was better than that of the control.

Accordingly, it is clear that the savor of boiled fish paste was modified and the quality of taste was improved by addition of the flavone derivative (I).

Therefore, it is clear that the flavone derivative (I) acts on modifying the savor (enhancing the savor).

Example 21

Modifying the savor (hard candy)_

Compound 10 of the flavone derivative (I) was used as a taste modifier, and 22.5 w/w % thick malt syrup of reducing maltose, 22.5 w/w % reducing starch saccharide and 0.08 w/w % of Aspartame were used as sweetening agents. In accordance with a general method, hard candy containing 0.0001 w/w % of the flavone derivative (I) and flavone derivative (I) free hard candy were prepared. Sensory tests for the savor were conducted by 10 panellers comprised of 6 males and 4 females at the age from 20 to 40.

As a result, all the panellers sensed that the savor of the flavone derivative (I)-containing hard candy was better than that of the control.

Accordingly, it is clear that the savor of hard candy was modified and the quality of taste was improved by addition of the flavone derivative (I).

Therefore, it is clear that the flavone derivatives (I) acts on modifying the savor (enhancing the savor).

Example 22

Modifying the body and the deliciousness (soft candy)

| | |
|---|---|
| Granulated sugar | 33.8 (g) |
| Thick malt syrup | 50.0 (g) |
| Gelatin | 2.0 (g) |
| Water | 10.0 (g) |
| Vegetable oils and fats (cacao oils and fats) | 11.0 (g) |
| Emulsifier (sucrose-fatty acid ester) | 1.0 (g) |
| Fondant paste | 1.0 (g) |
| Flavor | 0.2 (g) |
| Flavone derivative (I) | 0.00001 (g) |

Compound 1 of the flavone derivative (I) was used as a taste modifier. Gelatin which was swelled in advance with a part of water, followed by heating to dissolve, granulated sugar, thick malt syrup and the remaining water was mixed, followed by boiling down to 130° C. Then, fondant paste, vegetable oils and fats, emulsifier, colorant and the flavone derivative (I) were added thereto, thereby preparing flavone derivative (I)-containing soft candy. Alternatively, flavone derivative (I) free soft candy was prepared as a control by the same method.

Sensory tests for obtained soft candy were conducted by 8 panellers comprised of 6 males and 2 females at the age from 20 to 40.

The results are shown in Table 20.

TABLE 20

| | Sensory Test Results (number of people) | |
|---|---|---|
| Test items | Those who sensed the flavone derivative (I) additive is better | Those who sensed no difference |
| Body | 7 | 1 |
| Deliciousness | 8 | 0 |
| Quality of taste | 8 | 0 |

As seen from Table 20, it is clear that the body and the deliciousness of soft candy were enhanced and the quality of taste was improved by addition of the flavone derivative (I).

Therefore, it is clear that the flavone derivative (I) acts on modifying the body and the deliciousness (enhancing the body and the deliciousness).

Example 23

Modifying the body and the deliciousness (cookie)

| | |
|---|---|
| Cream cheese | 50 (g) |
| Powder sugar | 29 (g) |
| White sugar | 5 (g) |
| Citric acid (crystal) | 1 (g) |
| Flavor | 0.4 (g) |
| Colorant | 0.01 (g) |
| Flavone derivative (I) | 0.00002 (g) |
| Weak flour | 100 (g) |

-continued

| | | |
|---|---|---|
| Baking powder | 2 (g) | |
| Xanthan gum | 0.5 (g) | |
| Vegetable oils and fats | 40 (g) | |

Extract 1 of the flavone derivative (I) was used as a taste modifier. Cream cheese and powder sugar were kneaded, followed by adding white sugar and 50 w/w % citric acid solution (1 g of citric acid) and mixing until it is made smooth. Flavor, colorant and the flavone derivative (I) were added thereto. Then, a mixture comprising weak flour, baking powder, xanthan gum and vegetable oils and fats was further added thereto and mixed moderately, and allowed to stand in a refrigerator in one hour. Subsequently, it was molded and baked for 10 minutes at 170° C. to make cookie. Flavone derivative (I) free cookie was prepared in the same manner as a control.

Sensory tests for obtained cookie were conducted by 8 panellers comprised of 6 males and 2 females at the age from 20 to 40.

The results are shown in Table 21.

TABLE 21

| | Sensory Test Results (number of people) | |
|---|---|---|
| Test items | Those who sensed the flavone derivative (I) additive is better | Those who sensed no difference |
| Body | 7 | 1 |
| Deliciousness | 8 | 0 |
| Quality of taste | 6 | 2 |

As seen from Table 21, it is clear that the body and the deliciousness of cookie were enhanced and the quality of taste was modified by addition of the flavone derivative (I).

Therefore, it is clear that the flavone derivative (I) acts on modifying the body and the deliciousness (enhancing the body and the deliciousness).

Example 24

Modifying the body and the deliciousness (bread)

| | | |
|---|---|---|
| Sponge dough | Strong flour | 350 (g) |
| | Yeast food | 0.5 (g) |
| | Bread Yeast | 10 (g) |
| | Water | 300 (g) |
| Dough | Strong flour | 150 (g) |
| | Sugar | 30 (g) |
| | Salt | 10 (g) |
| | Powdered skim milk | 10 (g) |
| | Shortening | 20 (g) |
| | Water | 130 (g) |
| | Flavone derivative (I) | 0.00002 (g) |

Compound 5 of the flavone derivative (I) was used as a taste modifier. Strong flour, yeast food, bread yeast and water were mixed and fermented for four hours at 28° C. Dough materials comprising strong flour, sugar, powdered skim milk, shortening and water, and the flavone derivative (I) were added thereto and subjected to dough process, followed by baking for 25 minutes at 220° C., thereby preparing bread. Flavone derivative (I) free bread was prepared in the same manner as a control.

Sensory tests for obtained bread were conducted by 8 panellers comprised of 6 males and 2 females at the age from 20 to 40.

The results are shown in Table 22.

TABLE 22

| | Sensory Test Results (number of people) | |
|---|---|---|
| Test items | Those who sensed the flavone derivative (I) additive is better | Those who sensed no difference |
| Body | 7 | 1 |
| Deliciousness | 6 | 2 |
| Quality of taste | 7 | 1 |

As seen from Table 22, it is clear that the body and the deliciousness of bread were enhanced and the quality of taste was improved by addition of the flavone derivative Therefore, it is clear that the flavone derivative (I) acts on modifying the body and the deliciousness (enhancing the body and the deliciousness).

Example 25

Modifying the body and the deliciousness (casing boiled fish paste)

| | |
|---|---|
| Ground fish meat | 100 (g) |
| Salt | 2 (g) |
| Starch | 5 (g) |
| Water | 40 (g) |
| Flavone derivative (I) | 0.0001 (g) |

Compound 11 of the flavone derivative (I) was used as a taste modifier. Ground fish meat, salt, starch, water and the flavone derivative (I) were mixed. In accordance with a general method, casing boiled fish paste containing the flavone derivative (I) was prepared. Alternatively, flavone derivative (I) free casing boiled fish paste was prepared by the same method as a control.

Sensory tests for obtained casing boiled fish paste were conducted by 8 panellers comprised of 6 males and 2 females at the age from 20 to 40.

The results are shown in Table 23.

TABLE 23

| | Sensory Test Results (number of people) | |
|---|---|---|
| Test items | Those who sensed the flavone derivative (I) additive is better | Those who sensed no difference |
| Body | 6 | 2 |
| Deliciousness | 7 | 1 |
| Quality of taste | 7 | 1 |

As seen from Table 23, it is clear that the body and the deliciousness of casing boiled fish paste were enhanced and the quality of taste was improved by addition of the flavone derivative (I).

Therefore, it is clear that the flavone derivative (I) acts on modifying the body and the deliciousness (enhancing the body and the deliciousness).

Example 26

Modifying the body and the deliciousness (pickled NOZAWA-NA (Japanese phonetics) soaked with soy sauce)

| Soaked with soy sauce | |
|---|---|
| NOZAWA-NA previously soaked | 500 (g) |
| Soy sauce | 15 (g) |
| Sodium L-glutamate | 3 (g) |
| Sodium succinate | 0.2 (g) |
| Salt | 1 (g) |
| Water | 20 (g) |

| Seasoning base | |
|---|---|
| Water | 100 (g) |
| Salt | 5 (g) |
| Sodium L-glutamate | 0.6 (g) |
| Brewing vinegar | 4 (g) |
| Flavone derivative (I) | 0.00005 (g) |

Extract 1 of the flavone derivative (I) was used as a taste modifier. NOZAWA-NA previously soaked with soy sauce was moderately wrung out and packed into a bag with ½ amount of seasoning base, thereby preparing NOZAWA-NA soaked with soy sauce. Flavone derivative (I) free NOZAWA-NA soaked with soy sauce was prepared in the same manner as a control.

Sensory tests for obtained NOZAWA-NA were conducted by 8 panellers comprised of 6 males and 2 females at the age from 20 to 40.

The results are shown in Table 24.

TABLE 24

| | Sensory Test Results (number of people) | |
|---|---|---|
| Test items | Those who sensed the flavone derivative (I) additive is better | Those who sensed no difference |
| Body | 6 | 2 |
| Deliciousness | 7 | 1 |
| Quality of taste | 7 | 1 |

As seen from Table 24, it is clear that the body and the deliciousness of NOZAWA-NA soaked with soy sauce were enhanced and the quality of taste was improved by addition of the flavone derivative (I).

Therefore, it is clear that the flavone derivative (I) acts on modifying the body and the deliciousness (enhancing the body and the deliciousness).

According to the present invention, the flavone derivative (I) that is an active ingredient of the taste modifier of the present invention can modify various factors related to the taste. More particularly, it relates to the modification of enhancing the sourness, reducing the saltiness, inhibiting the brackish taste, inhibiting the unpleasant lasting of sweetness, enhancing the refreshing flavor and its continuity, reducing the flavor associated with, for example, acetic acid (stimulative smell associated with acetic acid), and enhancing the body, deliciousness and savor associated with the combination of the sourness, sweetness and flavor.

Therefore, the quality of taste can be modified by adding an effective amount of the flavone derivative (I) of the present invention to a product used in a mouth or orally ingestible product. Further, fruit taste or flavor can be sensed in fruit juice free products by adding the flavone derivative (I) that is an active ingredient of taste modifier of the present invention. Moreover, since the taste modifier of the present invention can enhance the sourness without increasing acid concentration, it is especially effective for adapting it to a product of which gelation generated by variation of pH or denaturation of protein causes problems.

What is claimed is:

1. A method of enhancing or reducing taste of an orally ingestible material that includes a substance therein of which an original taste is to be enhanced or reduced, without imparting bitterness to the orally ingestible material, comprising adding to the orally ingestible material an effective amount of at least one flavone derivative of the general formula (I) to enhance or reduce the original taste of the substance while not contributing a bitter taste to the orally ingestible material and allowing the original taste of the orally ingestible material to be sensed more pleasantly:

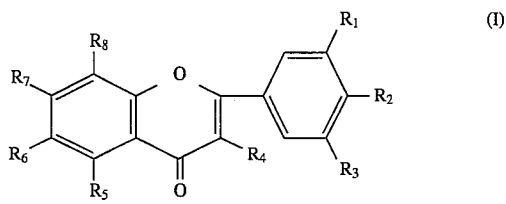

wherein $R_1$, $R_3$, $R_4$, $R_6$ and $R_8$ independently are a methoxy group or a hydrogen atom, $R_2$ and $R_7$ are methoxy groups, and $R_5$ is a methoxy group or a hydroxy group.

2. The method of enhancing or reducing taste according to claim 1, wherein the at lease one flavone derivative of the general formula (I) is present in the orally ingestible material in a concentration of 0.1 ppb to 1 ppm.

3. The method of enhancing or reducing taste according to claim 2, wherein the at least one flavone derivative of the general formula (I) is present in the orally ingestible material in a concentration of 1 ppb to 0.1 ppm.

4. The method of enhancing or reducing taste according to claim 1, wherein the orally ingestible material is in a form selected from the group consisting of chewing gum, buccal tablets and troches.

5. The method of enhancing or reducing taste according to claim 1, wherein the orally ingestible material comprises an edible material.

6. The method of enhancing or reducing taste according to claim 1, wherein the at least one flavone derivative enhances savor of the orally ingestible material.

7. The method of enhancing or reducing taste according to claim 1, wherein the orally ingestible material contains at least one member selected from the group consisting of an organic acid, phosphoric acid and phytic acid.

8. The method of enhancing or reducing taste according to claim 1, wherein the orally ingestible material contains menthol.

9. The method of enhancing or reducing taste according to claim 1, wherein the orally ingestible material contains acetic acid.

10. The method of enhancing or reducing taste according to claim 1, wherein the substance comprises a salty substance.

11. The method of enhancing or reducing taste according to claim 1, wherein the substance comprises a sweet substance.

12. The method of enhancing or reducing taste according to claim 1, wherein $R_5$ in the at least one flavone derivative (I) is an hydroxy group.

13. The method of enhancing or reducing taste according to claim 1, wherein $R_1$ to $R_6$ in the at least one flavone derivative (I) include 4 to 7 methoxy groups in total.

14. The method of enhancing or reducing taste according to claim 13, wherein all of $R_1$, $R_2$, $R_4$, $R_5$, $R_6$, $R_7$ and $R_8$ in the at least one flavone derivative (I) are methoxy groups and $R_3$ in the at least one flavone derivative (I) is an hydrogen atom.

15. The method of enhancing or reducing taste according to claim 1, wherein the at least one flavone derivative (I) is an extract extracted from a plant belonging to Rutaceae.

16. The method of enhancing or reducing taste according to claim 1, wherein the at least one flavone derivative (I) is at least one member selected from the group consisting of 3',4',5,6,7-pentamethoxyflavone, 3',4',5,6,7,8-hexamethoxyflavone, 4',5,6,7,8-pentamethoxyflavone, 3',4',5,7,8-pentamethoxyflavone, 3',4',5,7-tetramethoxyflavone, 5,7,8,4'-tetramethoxyflavone, 3,3'4',5,7,8-hexamethoxyflavone, 4',5,7-trimethoxyflavone, 5-hydroxy-4',6,7,8-tetramethyoxyflavone, 5-hydroxy-3',4',6,7,8-pentamethoxyflavone and 3,3',4',5,5',6,7,8-octamethoxyflavone.

17. The method of enhancing or reducing taste according to claim 16, wherein the at least one flavone derivative of the general formula (I) is present in the orally ingestible material in a concentration of 0.1 ppb to 1 ppm.

18. The method of enhancing or reducing taste according to claim 17, wherein the at least one flavone derivative of the general formula (I) is present in the orally ingestible material in a concentration of 1 ppb to 0.1 ppm.

19. The method of enhancing or reducing taste according to claim 1, wherein the orally ingestible material comprises a solid, and the at least one flavone derivative (I) comprises a powder.

20. The method of enhancing or reducing taste according to claim 1, wherein the orally ingestible material comprises a member selected from the group consisting of a liquid and a semi-solid, and the at least one flavone derivative (I) comprises a liquid.

* * * * *